United States Patent
Frugier et al.

(10) Patent No.: US 10,456,517 B2
(45) Date of Patent: Oct. 29, 2019

(54) INFUSION SITE FOR IMPROVED MIXING OF FLUIDS

(71) Applicant: GAMBRO LUNDIA AB, Lund (SE)

(72) Inventors: Alain Frugier, Tignieu (FR); Dominique Pouchoulin, Tramoyes (FR)

(73) Assignee: Gambro Lundia AB, Lund (SE)

( * ) Notice: Subject to any disclaimer, the term of this patent is extended or adjusted under 35 U.S.C. 154(b) by 257 days.

(21) Appl. No.: 15/680,336

(22) Filed: Aug. 18, 2017

(65) Prior Publication Data
US 2017/0340800 A1 Nov. 30, 2017

Related U.S. Application Data

(63) Continuation of application No. 14/262,413, filed on Apr. 25, 2014, now Pat. No. 9,827,366, which is a (Continued)

(30) Foreign Application Priority Data

Sep. 5, 2007 (FR) .................... 07 06204

(51) Int. Cl.
*A61M 1/00* (2006.01)
*A61M 1/36* (2006.01)
(Continued)

(52) U.S. Cl.
CPC ............ *A61M 1/3653* (2013.01); *A61M 1/34* (2013.01); *A61M 1/342* (2013.01);
(Continued)

(58) Field of Classification Search
CPC ........ A61M 1/3653; A61M 2025/0031; A61M 2001/3661; A61M 2001/3656; A61M 2025/0037
(Continued)

(56) References Cited

U.S. PATENT DOCUMENTS 3,916,892 A  11/1975  Latham, Jr.
4,280,496 A   7/1981  Van Baelen
(Continued)

FOREIGN PATENT DOCUMENTS

EP    0748635    12/1996
GB    1088565    10/1967
(Continued)

OTHER PUBLICATIONS

European Search Report for EP Application No. 16153825.1 dated May 4, 2016.
(Continued)

*Primary Examiner* — Andrew J Mensh
(74) *Attorney, Agent, or Firm* — K&L Gates LLP

(57) ABSTRACT

The invention relates to a blood line (108) comprising an infusion site (145) intended to inject into the line a solution comprising: —a first main channel (200) having a first passage section, —a second main channel (220) having a second passage section, —means for the formation (210) of a turbulence area located downstream from the first main channel, located upstream from the second main channel, these formation means comprising a first fluid passage means (224) defining a reduction (225) in the passage section and whose smallest passage section is smaller than the first passage section and smaller than the second fluid passage section, —a secondary channel (230) comprising an inlet (231) for letting in the solution and an outlet (232) in fluid communication with the first main channel or the means for the formation of a turbulence area or the second main channel.

24 Claims, 10 Drawing Sheets

2nd mode

Related U.S. Application Data continuation of application No. 12/674,110, filed as application No. PCT/IB2007/003297 on Oct. 31, 2007, now Pat. No. 8,715,217.

(51) Int. Cl.
*A61M 1/34* (2006.01)
*A61M 37/00* (2006.01)
*B01D 19/00* (2006.01)
*A61M 1/02* (2006.01)
*A61M 25/00* (2006.01)

(52) U.S. Cl.
CPC ........ *A61M 1/3413* (2013.01); *A61M 1/3431* (2014.02); *A61M 1/3434* (2014.02); *A61M 1/3437* (2014.02); *A61M 1/3458* (2014.02); *A61M 1/3659* (2014.02); *A61M 1/3672* (2013.01); *A61M 1/3675* (2013.01); *A61M 1/024* (2013.01); *A61M 1/3627* (2013.01); *A61M 25/0074* (2013.01); *A61M 2025/0031* (2013.01); *A61M 2202/0021* (2013.01); *A61M 2202/0042* (2013.01); *A61M 2206/16* (2013.01)

(58) Field of Classification Search
USPC ........... 422/44; 604/6.07, 6.09, 6.16; 96/209
See application file for complete search history.

(56) References Cited

U.S. PATENT DOCUMENTS

| | | | |
|---|---|---|---|
| 4,911,705 A | 3/1990 | Heinzerling et al. | |
| 5,188,603 A | 2/1993 | Vaillancourt | |
| 5,221,271 A * | 6/1993 | Nicholson | A61M 39/04 604/539 |
| 5,306,265 A * | 4/1994 | Ragazzi | A61M 39/02 128/912 |
| 5,512,043 A | 4/1996 | Verkaart | |
| 5,895,368 A | 4/1999 | Utterberg | |
| 5,983,947 A | 11/1999 | Utterberg | |
| 6,110,384 A | 8/2000 | Goux et al. | |
| 6,206,954 B1 | 3/2001 | Schnell et al. | |
| 6,685,664 B2 * | 2/2004 | Levin | A61M 1/34 210/321.6 |
| 6,986,751 B2 | 1/2006 | Villafana | |
| 7,223,336 B2 | 5/2007 | Tonelli et al. | |
| 7,556,060 B2 | 7/2009 | Guala | |
| 7,871,462 B2 * | 1/2011 | Yardimci | A61M 1/1658 96/208 |
| 2002/0007137 A1 | 1/2002 | Utterberg et al. | |
| 2004/0133145 A1 | 7/2004 | Bene | |
| 2005/0247203 A1 | 11/2005 | Chevallet | |
| 2005/0261637 A1 | 11/2005 | Miller | |

FOREIGN PATENT DOCUMENTS

| | | |
|---|---|---|
| JP | 3168160 | 7/1991 |
| WO | 0064456 | 11/2000 |
| WO | 2004000391 | 12/2003 |
| WO | 2004000391 A | 12/2003 |
| WO | 2004062721 | 7/2004 |
| WO | 2004082732 A2 | 9/2004 |

OTHER PUBLICATIONS

Grounds of Decision issued in Opposition proceeding in EP Application 07825554.4 on Jun. 7, 2018.

Hospal, Renal Intensive Care Global Marketing brochure dated Jul. 25, 2006. D4. Cited document in Opposition procedure for EP2183004 (Application No. 07825554.4).

Dialysprodukte und Medizintechnik (Dialysis Products and Medical Technology) (Serum-Werk Bernburg Vertriebs GmbH) brochure and English translation of same. Dated Mar. 3, 2001. D5. Cited document in Opposition procedure for EP2183004 (Application No. 07825554.4).

BVS—BlutVolumenSensor brochure and English translation of same. Dated Mar. 3, 2001. D6. Cited document in Opposition procedure for EP2183004 (Application No. 07825554.4).

Gambro Lundia AB brochure titled: "What are you looking for in a bloodline?" Copyright date 2005. D7. Cited document in Opposition procedure for EP2183004 (Application No. 07825554.4).

Dialysefibel 3, Individualitat, Flexibilitat und Qualitat in der Dialyse, Band 2, Mit Beitragen von et al., abakiss Verlagsgesellschaft GmbH, 2006. English translation of same. D13. Cited document in Opposition procedure for EP2183004 (Application No. 07825554.4).

Drukker, Parsons and Maher, "Replacement of Renal Function by Dialysis," 5th Edition, 2004. D14. Cited document in Opposition procedure for EP2183004 (Application No. 07825554.4).

Affidavit of Dr. Jorg Dreyhsig declaring public availability of document D13. Dated Mar. 12, 2018. D15. Cited document in Opposition procedure for EP2183004 (Application No. 07825554.4).

* cited by examiner

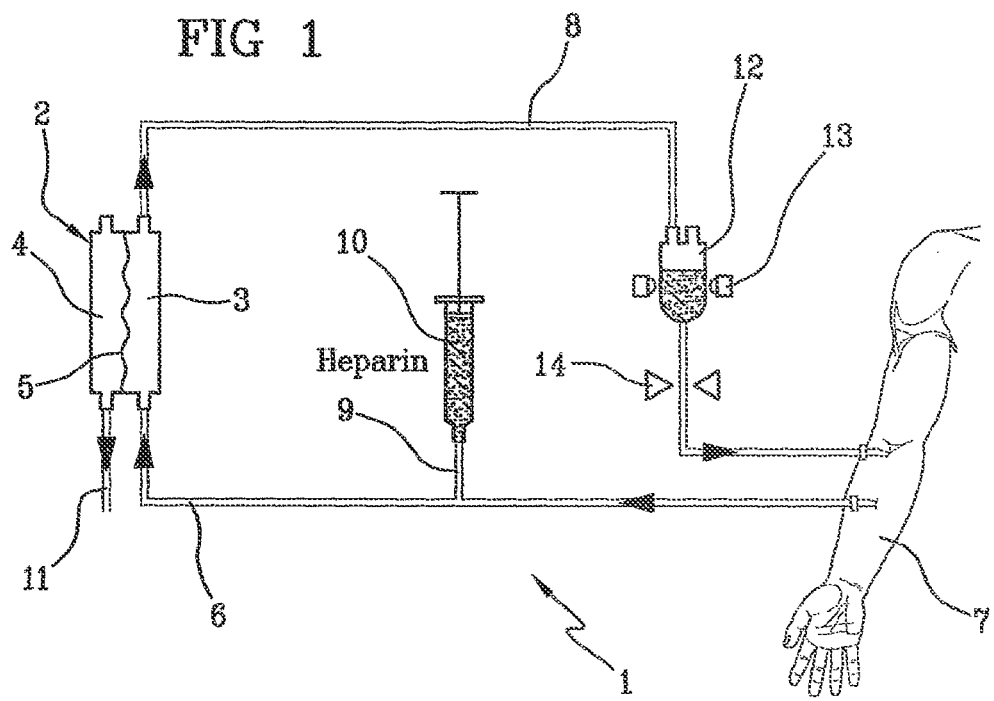
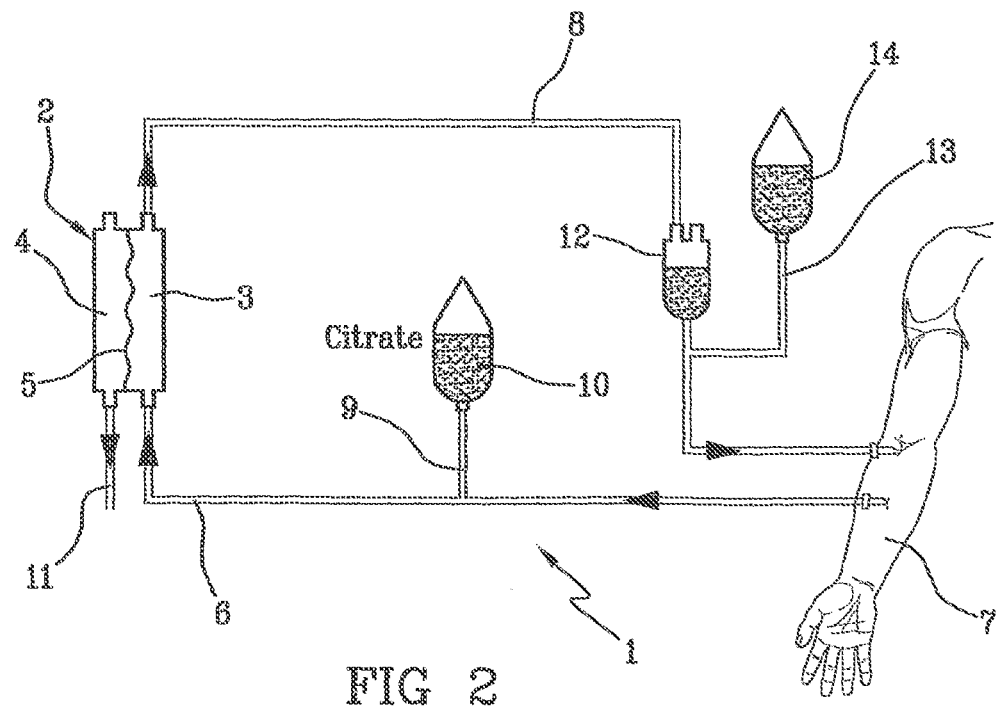

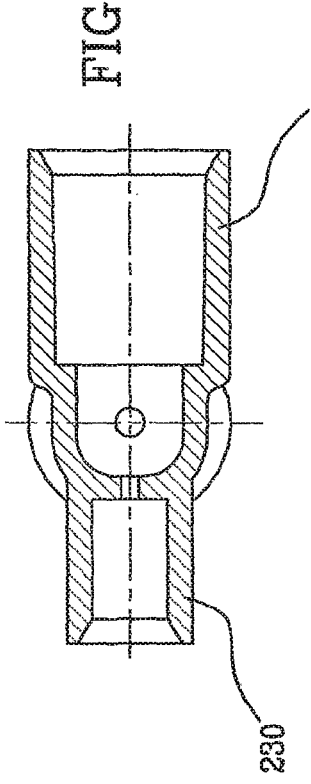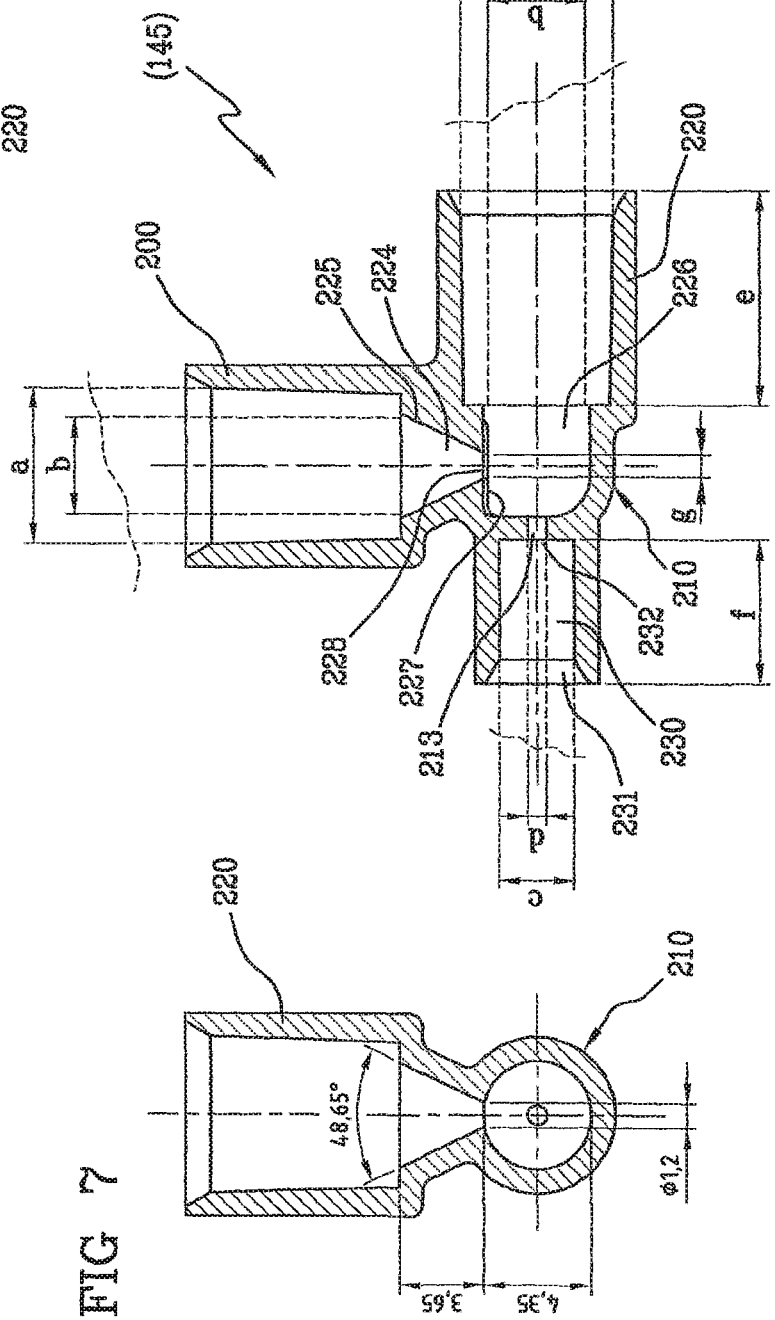

1st mode

2nd mode

2nd mode

3rd mode

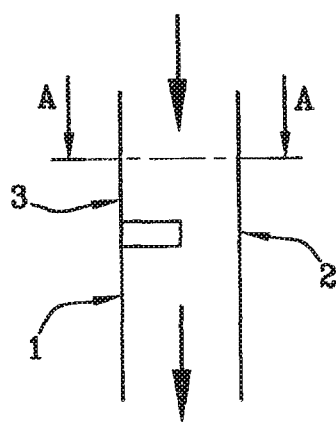
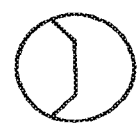
FIG 17
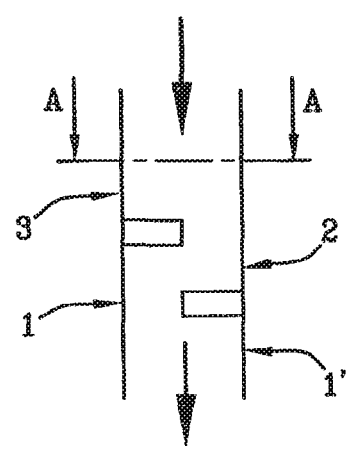
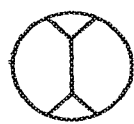
FIG 18
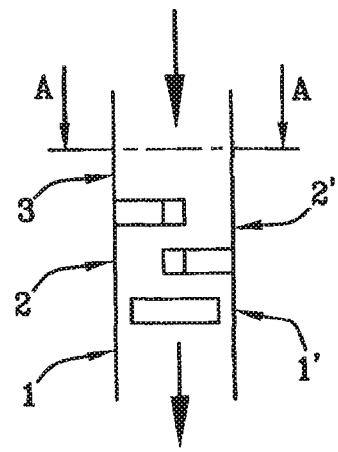
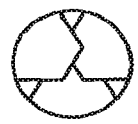
FIG 19
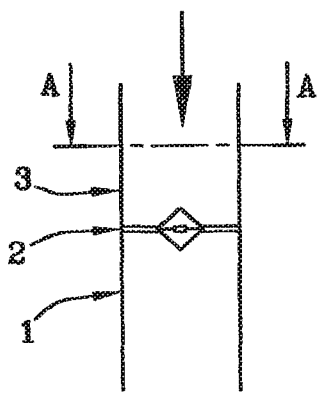
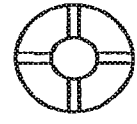
FIG 20
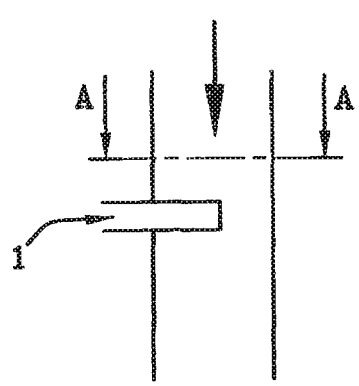
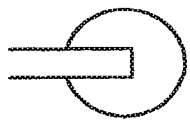
FIG 21
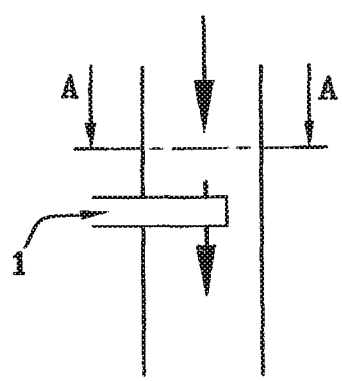
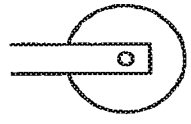
FIG 22

INFUSION SITE FOR IMPROVED MIXING OF FLUIDS

PRIORITY CLAIM

The present application claims priority to and the benefit as a continuation application of U.S. patent application Ser. No. 14/262,413, entitled "Infusion Site for Improved Mixing of Fluids", filed Apr. 25, 2014, which is a continuation of U.S. application Ser. No. 12/674,110, entitled "Infusion Site for Improved Mixing of Fluids", filed Feb. 18, 2010, now U.S. Pat. No. 8,715,217, issued May 6, 2014, which is a National Stage Entry of International Application No. PCT/IB07/003297, filed Oct. 31, 2007, which claims priority to FR 07/06204, filed Sep. 5, 2007, the entire contents of each of which are incorporated herein by reference and relied upon.

BACKGROUND

Technical Field of the Invention

The object of the present invention is a blood treatment device by way of extracorporeal circulation with anticoagulant pre-infusion, a disposable line to be used in an extracorporeal circuit for blood circulation with anticoagulant pre-infusion and a method for anticoagulation of blood treated by way of extracorporeal circulation.

Prior Art

Extracorporeal blood treatment is used for patients who are not able to effectively eliminate substances from blood, e.g. for a patient suffering from a temporary or permanent renal insufficiency. These patients and others can undergo a extracorporeal blood treatment so as to add or eliminate substances to or from blood, to keep an acid-base balance or to remove excess corporeal fluids for instance. Extracorporeal blood treatment is typically used for withdrawing undesired substances or molecules from a patient's blood and/or for adding beneficial substances or molecules to blood.

Extracorporeal blood treatment is typically carried out by withdrawing blood from the patient continuously, introducing blood into a main compartment of a filter, in which blood gets through a semipermeable membrane (see FIG. 3). The semipermeable membrane lets undesired substances contained in blood through in a selective manner, from the main to the secondary compartment, and also lets beneficial substances contained in the liquid in the secondary compartment through in a selective way, to blood getting through the main compartment, depending on the type of treatment.

A number of extracorporeal blood treatments can be carried out with the same machine. In an ultrafiltration treatment (UF), the undesired substances are removed from blood by convection through the membrane in the secondary compartment.

In a hemofiltration treatment (HF), blood flows through the semipermeable membrane as in UF, and beneficial substances are added to blood, typically by introducing a fluid into blood, both before and after it gets through the filter and before it is returned to the patient.

In a hemodialysis treatment (HD), a secondary fluid containing beneficial substances is introduced into the secondary compartment of the filter. The undesired substances contained in blood get through the semipermeable membrane and into the secondary fluid, and the beneficial substances can get from the secondary fluid through the membrane into blood.

In a hemodiafiltration treatment (HDF), blood and the secondary fluid exchange their substances as for HD, and moreover substances are added to blood, typically introducing a fluid into treated blood before the latter is returned to the patient as for HF.

For carrying out a hemodialysis, hemofiltration or hemodiafiltration session, blood circulating in the extracorporeal circulation line has to undergo an anticoagulation treatment so as to prevent blood contacting synthetic material (circulation lines, fibers of the dialyzer) from coagulating. Most often, this anticoagulation occurs with heparin, which is known for its anticoagulant properties. Heparin is injected in pre-infusion into the arterial line of the device and is thus present in the whole extracorporeal blood circuit, •from pre-infusion up to blood return into the patient. As a consequence, heparin doses are administered to the patient through the blood return line. Even if coagulation should be prevented in the extracorporeal circulation line, in some cases the risk of bleeding for the patient can represent a danger. It is especially the case of highly hemorrhagic patients (e.g. in the days following a major surgical operation) or also of patients that are hypersensitive to heparin. The anticoagulation treatment with heparin can therefore prove to be dangerous for the patient due to heparin injection through the blood return line to the patient.

FIG. 1 shows a blood treatment device by way of extracorporeal circulation 1 at the state of the art, comprising a filter 2 having a first compartment 3 and a second compartment 4 separated by a semipermeable membrane 5. The device includes •an arterial line 6 connected to the first compartment 3 of the filter for circulating blood taken from a patient 7, and a venous line 8 getting out of the first compartment of the filter. A pre-infusion channel 9 is connected to a container 10 containing a heparin solution and is attached to the arterial line 6, the solution having the purpose of preventing blood from coagulating outside the patient's body, a drain channel 11 getting out of the second compartment 4 of the filter. An air separator 12 is attached to the venous line 8. The air separator 12 includes also an air detector 13, and a clamp 14 is placed on the venous line 8 downstream from the air separator 12, i.e. downstream in the sense of blood circulation in the venous line 8. The clamp enables to stop blood flow if air bubbles are detected by the detector 13 before blood is returned to the patient 7.

The heparin solution, as mentioned above, acts against blood coagulation both in the whole device 1 and in the patient's body. Therefore, heparin return and injection into the patient's body 7, can prove to be dangerous.

Patent application PCT/EP00/03583, whose hydraulic circuit is shown in FIG. 2, relates to an substitution infusion fluid, especially for use in blood hemofiltration, and to a citrate anticoagulant solution for local anticoagulation. In order to prevent blood coagulation, during a hemodialysis session, it is known that citrate ions can be used as anticoagulant.

Citrate ions, added to blood in the extracorporeal circuit before getting into the artificial kidney, act as anticoagulants thanks to their ability of chelating calcium ions. During hemofiltration, a part of citrate ions (mainly those chelated with blood calcium) gets through the artificial kidney. This appreciable calcium loss is compensated by a post-filter or systemic calcium infusion. Citrate ions act as anticoagulants only in the extracorporeal circuit, since when they get into the patient's systemic circulation, they are rapidly metabolized into bicarbonate ions. The risk of bleeding complications due to systemic anticoagulation is avoided. In FIG. 2, the device 1 comprises a filter 2 having a first compartment 3 and a second compartment 4 separated by a semipermeable membrane 5. The device includes an arterial line 6 connected to the first compartment 3 of the filter for circulating blood taken from a patient 7, and a venous line 8 getting out of the first compartment of the filter. A pre-infusion channel 9 containing an anticoagulant, trisodium citrate, is connected to a container 10 including a solution of citrate ions attached to the arterial line 6, the solution having the purpose of preventing blood from coagulating outside the patient's body. A drain channel 11 is attached at the outlet of the second compartment 4 of the filter and an air separator 12 is attached to the venous line 8. The venous line 8 includes, beyond the bubble trap 12, a channel 13 connected to a container 14 containing a solution reestablishing blood ion balance. As a matter of fact, the citrate solution makes blood anticoagulable by decalcifying it upstream from the filter. This channel 13 is attached downstream from the bubble trap 12, i.e. downstream in the sense of blood circulation in the venous line 8 before blood is returned to the patient 7.

As a matter of fact, in order to reestablish a correct hemostasis, blood ion balance has to be reestablished—especially by recalcifying it—at the outlet of the filter.

It is known to carry out this infusion of solution reestablishing ion balance also by injecting calcium into a bubble trap present on the venous line.

As an alternative, it is eventually known to carry out this infusion of solution reestablishing blood balance directly in a patient's vascular access separated from the extracorporeal circuit (not shown). With respect to the first technique, the drawback of this second technique consists in the need for an independent control of the pump or syringe administering citrate by infusion and of the pump administering the solution reestablishing ion balance by infusion.

We shall refer to the technique consisting in infusing the reestablishing solution into the blood extracorporeal circuit. This technique makes use of a bubble trap present on the venous line or a simple infusion site present on the venous line.

Such an infusion site is generally made up of a main channel having the same diameter as the blood line, and of a secondary channel having a smaller diameter, attached perpendicularly on the main channel on one side and comprising a secondary inlet site for the infusion liquid. This secondary inlet site can be an "empty" channel where the liquid gets through or a channel provided in its section with a membrane apt to be pierced by the needle of a syringe containing the solution to be infused.

The Applicant has made in-vitro and in-vivo tests on sheep models for extracorporeal circulation with a citrate anticoagulation on the arterial line (in pre-infusion) and a calcium injection on the venous blood line (in post-infusion). First tests have been carried out by infusion of ion reestablishing solution directly into the bubble trap of the venous line of the extracorporeal circuit, and other tests have been carried out with a traditional infusion device located on the venous line.

A recurrent problem related to the mixing of the reestablishing solution with dialyzed blood has been observed: this mixing does not occur uniformly and there are significant local coagulation problems, which become evident especially with the appearance of coagulation filaments.

Therefore, there was the need to provide a solution so that the infusion of reestablishing solution has a significantly reduced coagulation. To this purpose, the inventors have thought to optimize the mixing of dialyzed blood of the venous line and calcium injected into the venous line Disclosure of the Invention The goal of the present invention is to solve this problem concerning coagulation in the blood extracorporeal circuit due to the infusion of the solution reestablishing ion balance.

To this purpose, the invention related to a blood line (108) for extracorporeal blood or plasma. treatment comprising:
  a first line portion (134) intended to be connected to the outlet of a filter,
  a second line portion (137) intended to be connected to a patient's vascular access,
  an infusion site (145) acting between the first line portion (134) and the second line portion (137), and intended to inject into the blood line a solution reestablishing blood or plasma ion balance, comprising:
  a first main channel (200) in fluid communication with the first line portion (134) and having a first passage section,
  a second main channel (220) in fluid communication with the second line portion (137) and having a second passage section,
  means for the formation (210) of a turbulence area located downstream from and in fluid communication with the first main channel, located upstream from and in fluid communication with the second main channel, these formation means comprising a first fluid passage means (224) defining a reduction (225) in the passage section and whose smallest passage section is smaller than the first passage section and smaller than the second fluid passage section,
  a secondary channel (230) comprising an inlet (231) for letting in a solution reestablishing ion balance and an outlet (232) in fluid communication with at least one of the three elements chosen among the first main channel (200), the means for the formation (210) of a turbulence area and the second main channel (230).

The blood line is preferably used as venous line.

The invention also relates to a set of lines intended to be attached to a blood or plasma filter (102) comprising:
  an arterial line (106) having a connector intended to be connected to the first compartment (103) of a filter (102),
  a pre-infusion channel (109) for a local anticoagulation substance attached to the arterial line (106),
  a blood line (108) according to the invention, wherein the inlet (135) of the first line portion (134) is intended to be connected to the outlet of the filter (102) and the outlet of the second blood portion line (137) is intended to be connected to a patient's vascular access.

The invention also relates to a blood or plasma treatment device by way of extracorporeal circulation (101) comprising:
  a filter (102) having a first (103) and a second (104) compartment separated by a semipermeable membrane (105),
  an arterial line (106) connected to the first compartment (103) of the filter (102),
  a pre-infusion channel (109) for a local anticoagulation substance attached to the arterial line (106),
  characterized in that it comprises a blood line (108) getting out of the first compartment (103) of the filter (102) according to the invention.

Eventually, the invention relates to a method for extracorporeal blood treatment carried out with the device according to the invention, including the following steps:

a) making blood or plasma flow through the arterial line (106), b) infusing through the pre-infusion channel (109) a local anticoagulation substance in the arterial line (106), c) filtering blood through the filter (102), d) making filtered blood flow through the first portion of the blood line (108), e) making filtered blood flow in a reduction of the passage section of the infusion site, thus causing a turbulence in blood flow, f) infusing through the secondary channel (230) of the infusion site (145) a solution for reestablishing ion balance, g) making filtered blood mixed with the solution for reestablishing ion balance flow through the second portion of the blood line (108), wherein step f) is carried out straight before, during or straight after step e).

SHORT DESCRIPTION OF THE DRAWINGS

Further advantages and characteristics of the invention shall emerge from the following description.

We shall make reference to the attached drawings, wherein:

FIG. 1 shows the state of the art concerning an apparatus for extracorporeal blood treatment with anticoagulation prevention by way of heparin;

FIG. 2 shows the state of the art concerning an apparatus for extracorporeal blood treatment with anticoagulation prevention by way of citrate;

FIGS. 5, 6 and 7 show in detail the injection site according to a first embodiment of the invention, in sectioned front view, sectioned top view and sectioned right view, respectively

FIGS. 17, 18, 19, 20, 21 and 22 show diagrams of embodiments of the infusion site with partial separations, their A-A section being in view;

DETAILED DISCLOSURE OF EMBODIMENTS OF THE INVENTION

Figure 3:
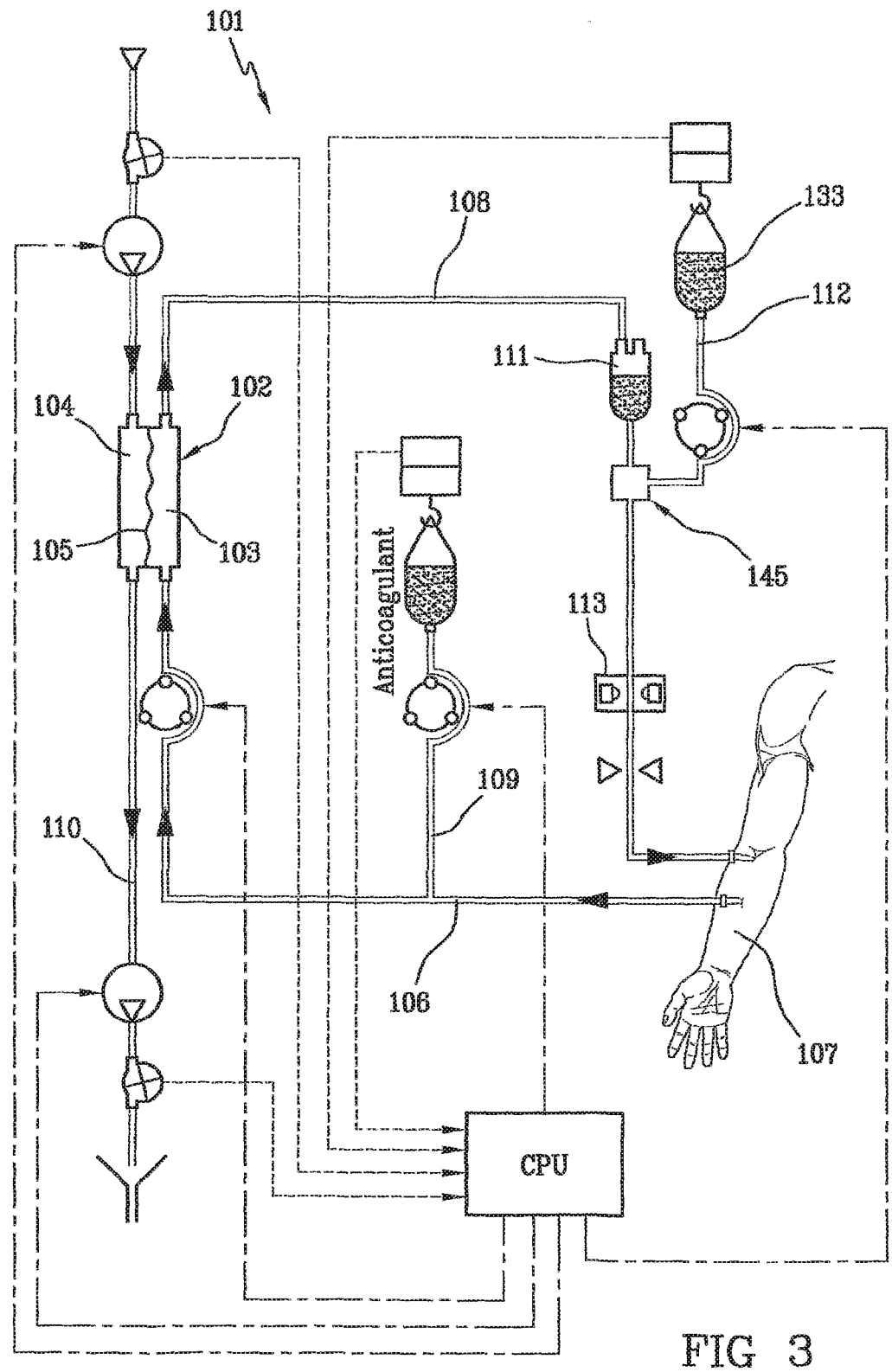
FIG. 3 shows the blood treatment device by way of extracorporeal circulation according to the invention.

FIG. 3 shows the blood treatment device by way of extracorporeal circulation according to the invention, intended to carry out a dialysis treatment. The blood treatment device by way of extracorporeal circulation 101 according to the invention comprises a filter 102 having a first 103 and a second compartment 104 separated by a semipermeable membrane 105. Depending on the membrane, the filter (105) can be a hemofilter, a plasma filter, a dialyzer or a filter of other type. As far as the membrane is concerned, membranes used are hollow fiber membranes or plate or sheath membranes. An arterial line 106 is connected to the first compartment 103 of the filter for circulating blood taken from a patient 107. A blood line 108 is connected at the outlet of the first compartment 103 of the filter. A pre-infusion channel 109 for a local anticoagulation substance is attached to the arterial line 106. A drain channel 110 is connected at the outlet of the second compartment 104 of the filter. An air separator 111 is placed on the blood line 108 and a post-infusion line 112 for a solution at least partially reestablishing blood ion balance is located downstream—i.e. downstream in the sense of blood circulation in the blood line 108—from the air separator 111. Eventually, an air detector 113 is located downstream from the post-infusion line 112.

It should be noted that FIG. 3 shows a treatment mode by way of dialysis, though the invention applies to all types of extracorporeal blood treatments mentioned above: hemofiltration, hemodiafiltration and so on, which can actually be implemented with a citrate anticoagulation.

Figure 4:
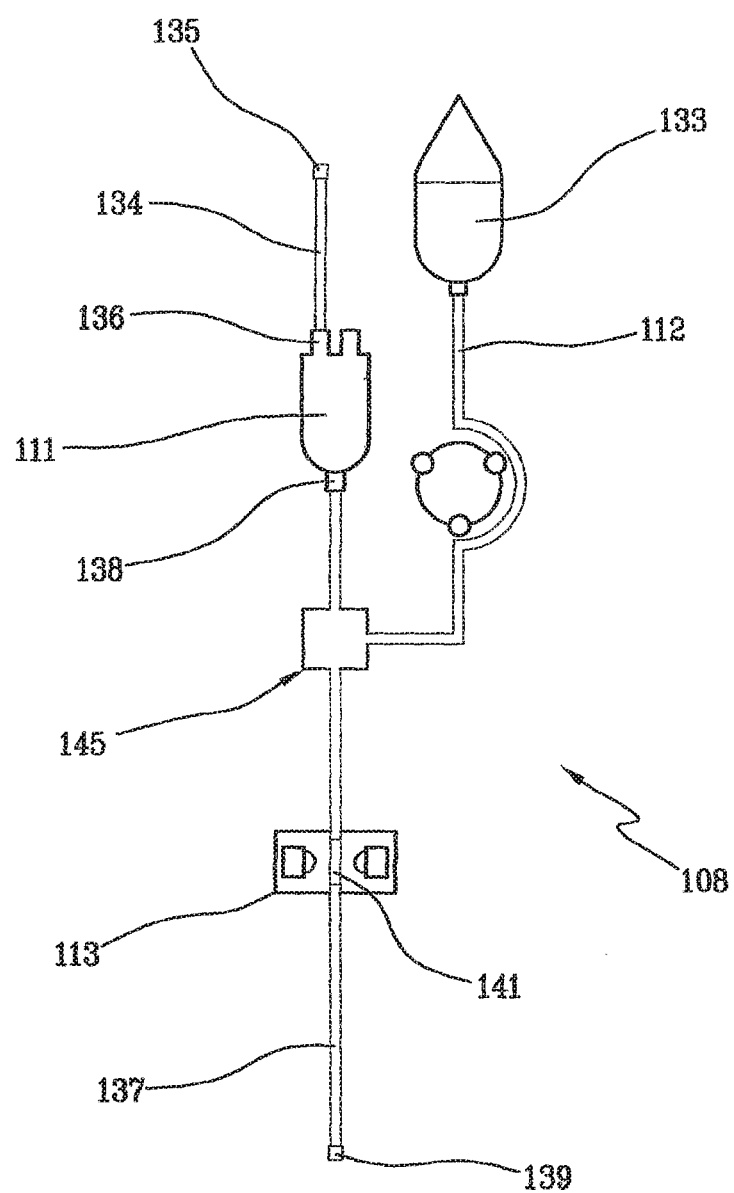
FIG. 4 shows a disposable line for blood treatment by way of extracorporeal circulation according to the invention.

FIG. 4 shows the disposable blood line 108 for use in a circuit for the extracorporeal circulation of blood having undergone a pre-infusion of anticoagulant, comprising a first channel 134 with a first connection 135 for attaching a filter, and a second connection 136. An air separator 111 is attached to the second connection 136 downstream—i.e. downstream in the sense of blood circulation—from the first channel 134. The disposable blood line 108 also comprises a second channel 137 having a third connection 138 for attaching the outlet of the air separator 111, and a fourth connection 139 for attaching a patient's blood access.

The infusion site 145 is intended to receive a post-infusion line 112 for a solution at least partially reestablishing blood ion balance and is in fluid communication with the second channel 137 and in fluid communication with the channel 134. The line further includes a first portion 141 of the second channel 137 that is able to cooperate with the air detector 113 and placed downstream from the site 145. The first portion 141 is optically coded, e.g. with different colors, with a relief, with a pipe having a different material, shape or size with respect to the remaining line. The above described elements of the line are not strictly necessary for implementing the invention, either.

FIG. 4 shows the infusion site 145 located between the bubble trap 111 and the first portion 141 of the second channel 134. In this case, the site is placed in the sense of blood circulation—upstream from the air detector 113 and the air detector enables to monitor an undesired air introduction, if any, into the circuit towards the patient.

However, as an alternative to the configuration of FIG. 4, the infusion site can be located on the blood line downstream from the first portion 141 that is able to cooperate with the air detector 113. In this case, the infusion line 112 is provided with a self-degassing filter enabling to place the connection of the line 112 as desired on the line 137, especially as close as possible to the connector 139, which makes the presence of the detector 113 on the line 137 useless for the infusion line 112.

Figure 8:
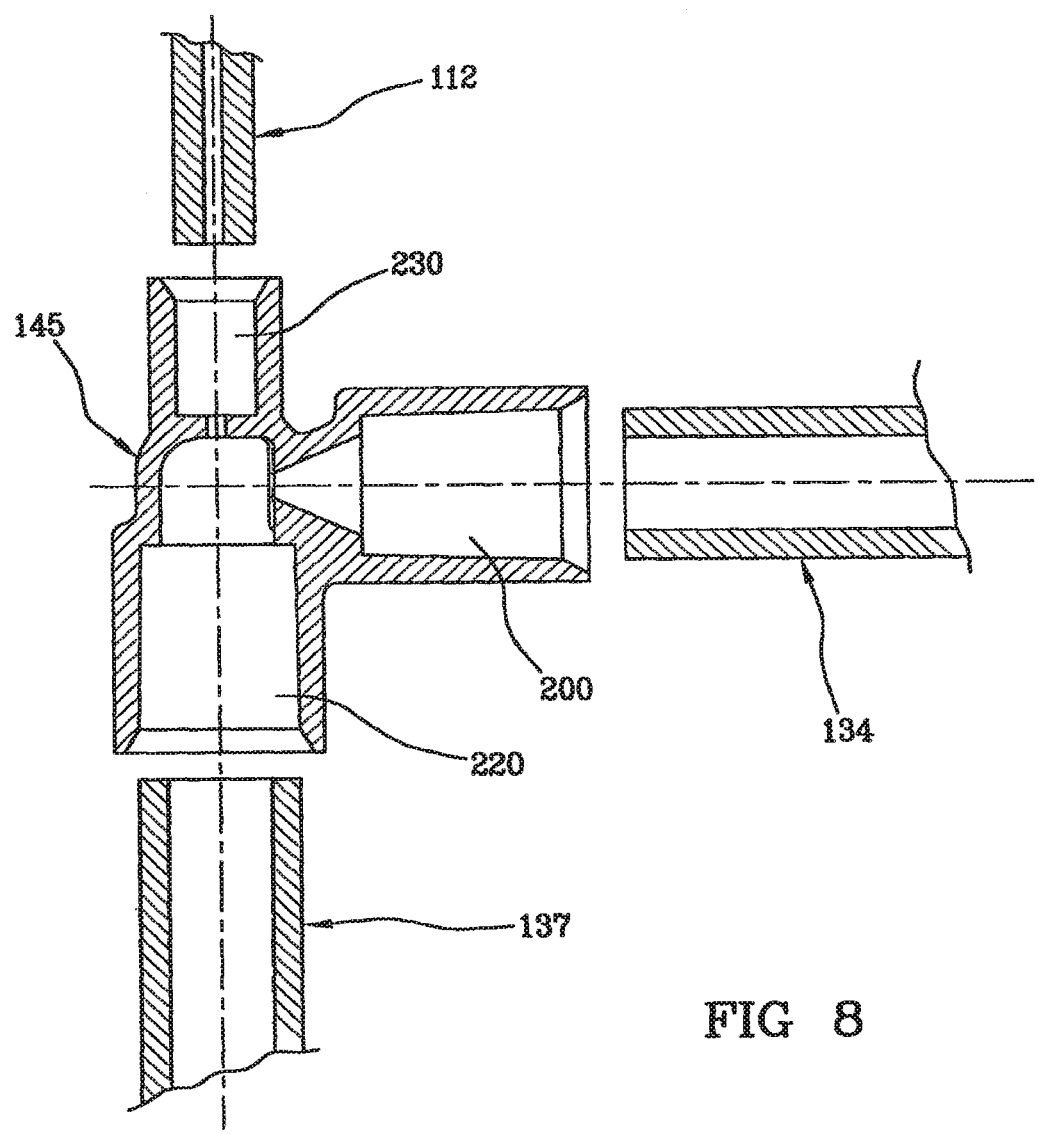
FIG. 8 shows in detail the injection site according to a first embodiment connected to a portion of the blood line, in exploded and sectioned front view.
Figure 11:
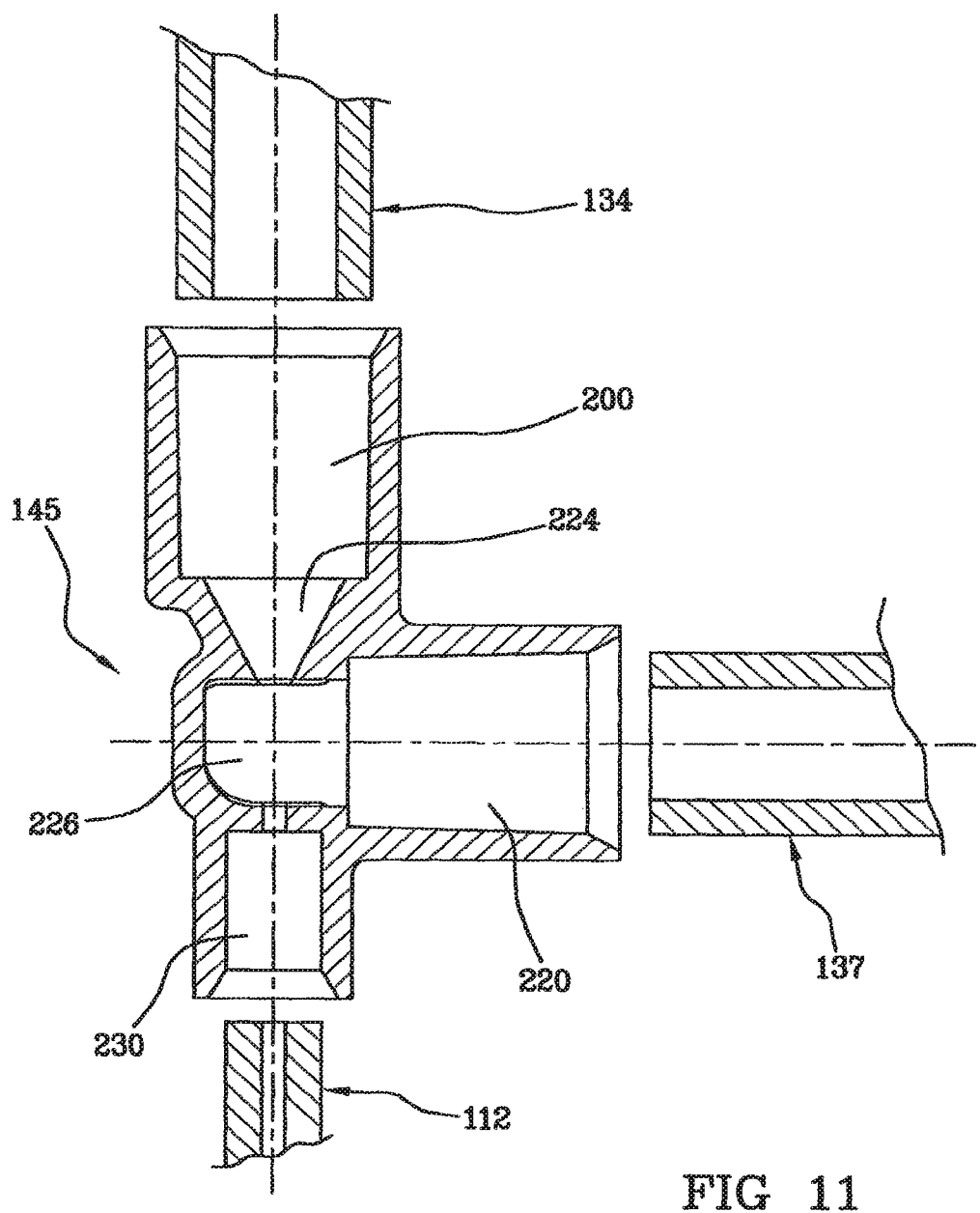
FIG. 11 shows in detail the injection site according to a second embodiment connected to a portion of the blood line, in exploded and sectioned front view.
Figure 12:
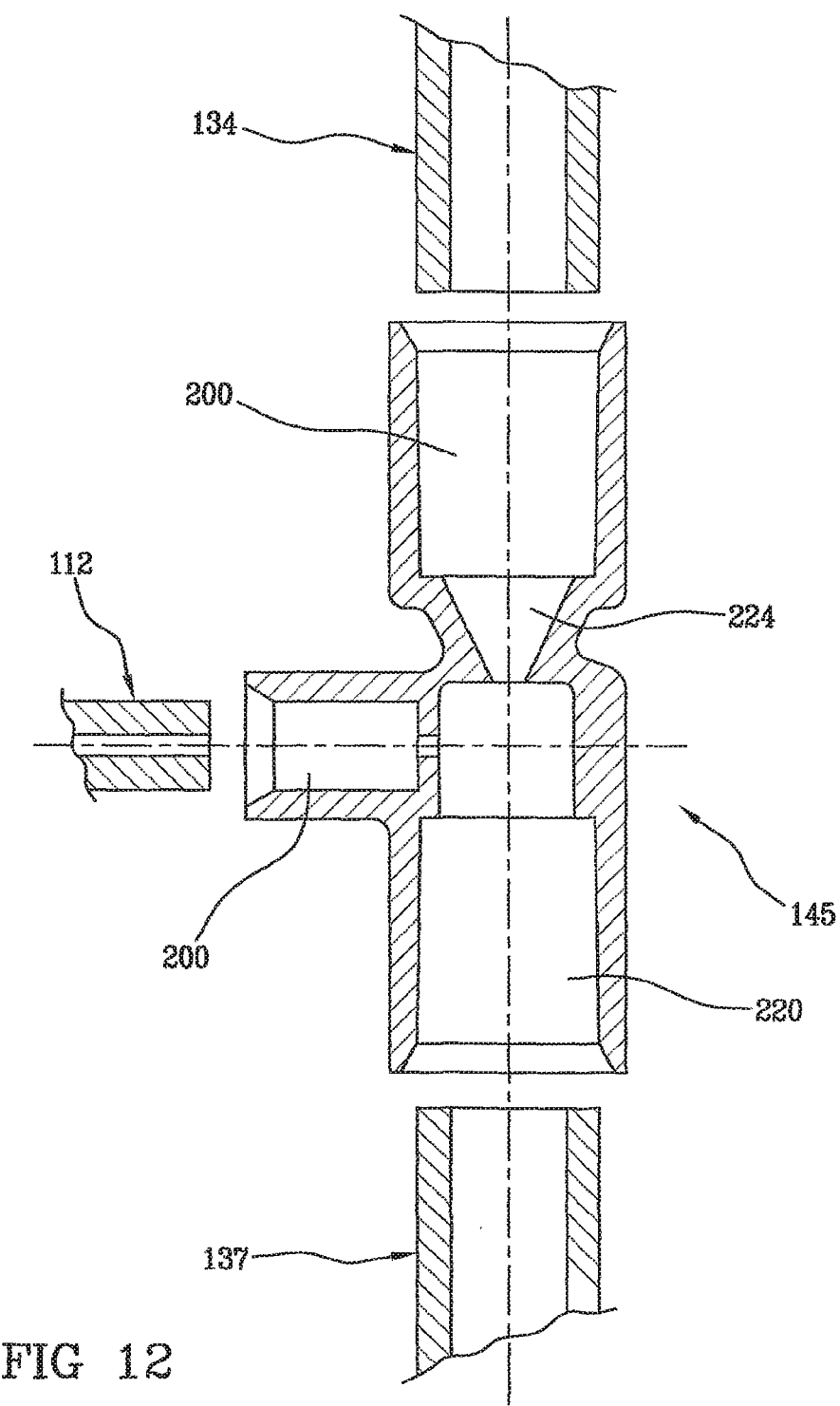
FIG. 12 shows in detail the injection site according to a third embodiment connected to a portion of the blood line, in exploded and sectioned front view.

As shown on each of the FIGS. 8, 11 and 12, the invention is a blood line (108) for extracorporeal blood or plasma treatment, comprising:

a first line portion (134) intended to be connected to the outlet of a filter, a second line portion (137) intended to be connected to a patient's vascular access, an infusion site (145) acting between the first line portion (134) and the second line portion (137), and intended to inject into the blood line a solution reestablishing blood or plasma ion balance, comprising:

a first main channel (200) in fluid communication with the first line portion (134) and having a first passage section, a second main channel (220) in fluid communication with the second line portion (137) and having a second passage section, means for the formation (210) of a turbulence area located downstream from and in fluid communication with the first main channel, located upstream from and in fluid communication with the second main channel, these formation means comprising a first fluid passage means (224) defining a reduction (225) in the passage section and whose smallest passage section is smaller than the first passage section and smaller than the second fluid passage section, a secondary channel (230) comprising an inlet (231) for letting in a solution reestablishing ion balance and an outlet (232) in fluid communication with at least one of the three elements chosen among the first main channel (200), the turbulence area formation means (210) and the second main channel (230).

The assembly of the channels with the infusion site is not shown in FIGS. 8, 11 and 12 since the device is in an exploded view. Conversely, the device in FIG. 5 shows the finished device according to the assembly mode of the invention. The pipes are assembled by way of internal mounting. Assembly can be carried out by gluing mainly with a solvent or with radiation (e.g. UV) polymerizing glue.

In order to optimize the mixing homogeneity of blood and calcium, the geometry of the infusion site has been given the first place so as to enable the formation of a blood turbulence area integrated into the blood flow area. Indeed, it is important to increase the number of Reynolds so as to ensure the switch from a laminar flow to a turbulent flow in the injection site, which means homogenization of the two liquids and prevents local coagulation due to an inaccurate mixing.

According to the invention, blood reaches this flow rate in the infusion site and should be able to get out of it with the same flow rate per hour, and preferably substantially the same linear flow rate (ml/mm) after getting through the turbulence area (the smallest infusion flow rate as possible is added to the inlet flow rate).

A turbulence area is an area in which fluid flow becomes instable and perturbed, thus generating multiple whirlpools. The turbulent flow is opposed to the laminar flow. Reducing the passage section in the infusion site enables to increase the number of Reynolds to a sufficient degree so as to switch from a laminar to a turbulent flow, so as to generate a turbulence, though leaving hemoglobin untouched and ensuring the prescribed blood flow rate. As a matter of fact, it should be noted that hemoglobin, more precisely red corpuscles, are not damaged during treatment, which enables to prevent a hemolysis that might be fatal to the patient. Moreover, the blood flow rate should keep a given threshold in order to prevent the treatment from getting longer.

Therefore, the solution enabling to reestablish ion balance (e.g. calcium) is injected directly close to the turbulence formation area. The turbulence formation area gets integrated into the disposable blood line. Once more, turbulence intensity is optimized so as to ensure at the same time a sufficient mixing and to prevent a significant hemolysis in the expected operating range.

The comparative tests on the infusion site according to the invention show highly positive results since the mix is homogenized without altering any other treatment parameters. As a matter of fact, calcium infusion close to the blood turbulence area inhibits the long threads of fibrins observed on a prior art infusion site and no clots are observed, either. Tests have been carried out by periodically monitoring coagulation time (APTT) and calcium, sodium and potassium as well as pH.

The turbulence area formation means (210) can comprise a secondary inlet (213), and the outlet (232) of the secondary channel of the site (230) is connected to said secondary inlet (213).

Alternatively, the first main channel (200) can include a secondary inlet (shown schematically by arrow 3 in FIGS. 13 to 20), and the outlet (232) of the secondary channel of the site (230) is connected to said secondary inlet (arrow "3"). In this case, the outlet (232) of the secondary channel of the site (230) is connected to said secondary inlet (213) straight downstream from the turbulence area formation means.

Still alternatively, the second main channel (220) includes a secondary inlet (shown schematically by the arrows "1" and "1'" in FIGS. 13 to 20), and the outlet (232) of the secondary channel of the site (230) is connected to said secondary inlet (1, 1'). In this case, the outlet (232) of the secondary channel of the site (230) is connected to said secondary inlet (213) straight upstream from the turbulence area formation means.

Continuous Section Narrowing:

Moreover, the first fluid passage means (224) of the turbulence area formation means (210) can define a continuous section narrowing in the sense of fluid passage. More particularly, the first fluid passage means (224) of the turbulence area formation means (210) defined a constant narrowing of internal circular section, thus resulting in an internal conical surface of revolution whose symmetry axis is the longitudinal axis of the 10 first passage means. It has been shown that a constant, smooth, continuous and preferably progressive narrowing enables not to limit hemolysis intensity. The number of Reynolds in the surface of the smallest circular section (228) of the conical surface can be chosen depending of the expected operating range of the device. The number of Reynolds for a blood passage in the smallest circular section of the conical surface (228) can vary from about 500 to about 2,000.

Figure 9:
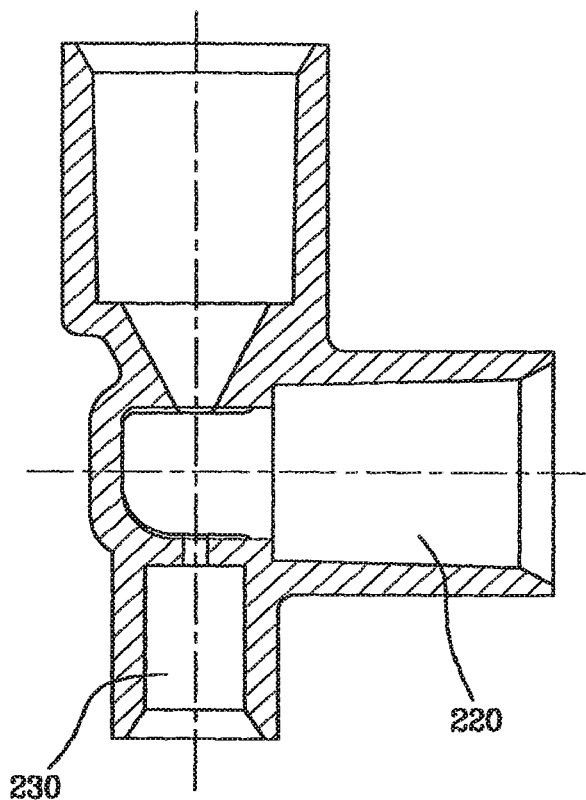
FIGS. 9 and 10 show in detail the injection site according to a second embodiment of the invention, in sectioned front view and sectioned left view, respectively.
Figure 10:
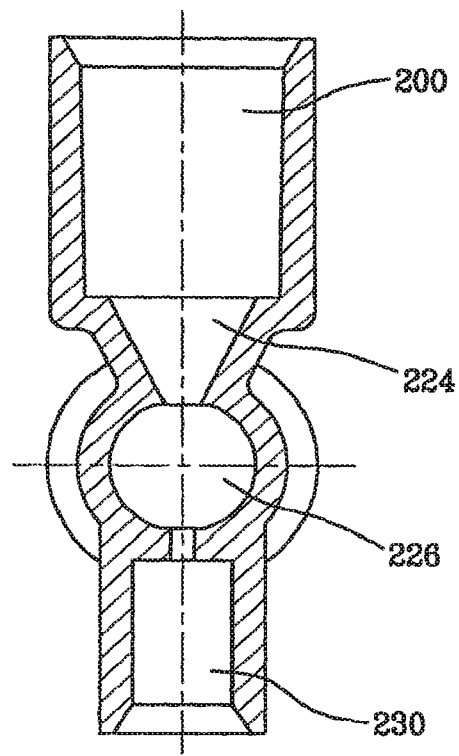

Operating Range:

The number of Reynolds is chosen so as to obtain a compromise between homogeneous mixing and hemolysis prevention as a function of the blood flow rate range. The development of the number of Reynolds in section "g" for the two sizes of the components (calculation for a viscosity of 3 cP) is shown in the following table:

| Blood flow rate ml/min. | High flow version (FIGS. 5, 6 and 7) | Low flow version (FIGS. 9 and 10) |
| --- | --- | --- |
| 50 | | 442 |
| 75 | | 663 |
| 100 | 590 | 880 |
| 150 | 880 | 1,330 |

| Blood flow rate ml/min. | High flow version (FIGS. 5, 6 and 7) | Low flow version (FIGS. 9 and 10) |
|---|---|---|
| 20 | 1,180 | 1,770 |
| 250 | 1,470 | |
| 300 | 1,770 | |
| 350 | 2,060 | |

However, this table should not be deemed as limiting. The number of Reynolds can vary in the range [350, 3,000), preferably in the range [500, 2,000].

Furthermore, as is still shown in at least FIGS. 5 to 12, the turbulence area formation means (210) can include a second fluid passage means (226) downstream from the first fluid passage means (224) defining an increase (227) in the fluid passage section in the sense of fluid passage. More particularly, the largest fluid passage section of the second fluid passage means (226) shall be smaller than said first passage section and smaller than said second passage section. Thus, the increase (227) in the fluid passage section of the second fluid passage means (226) can define a shoulder perpendicular to the axis of the second fluid passage means (224).

Generally speaking, FIGS. 13 to 16 show turbulence area formation means comprising a constant narrowing of the blood passage section. The first and second main channels of the site are shown with an arrow indicating the sense of blood passage. Three alternative preferred positions of the inlet of the secondary channel into the main channels of the site which blood gets through are shown by numerals 1, 2 and 3. "1" corresponds to injection straight downstream from the blood turbulence formation area; "2" corresponds to injection in the blood turbulence formation area, and "3" corresponds to injection straight upstream from the blood turbulence formation area.

Figure 13:
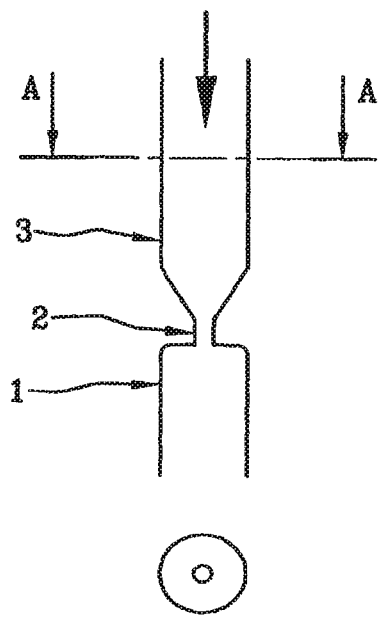
FIGS. 13, 14, 15 and 16 show diagrams of embodiments of the infusion site with constant section narrowing, their A-A section being in view.

In FIG. 13 the turbulence area formation means comprise a constant narrowing according to the longitudinal axis of the site, then a short pipe portion with small diameter and, eventually, a shoulder enabling to get back to the starting diameter of the site and of the blood line.

Figure 14:
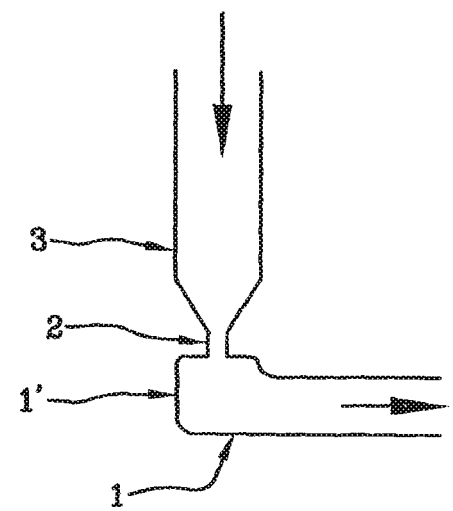

FIG. 14 shows the same site as in FIG. 13 with a perpendicular elbow pipe.

Figure 15:
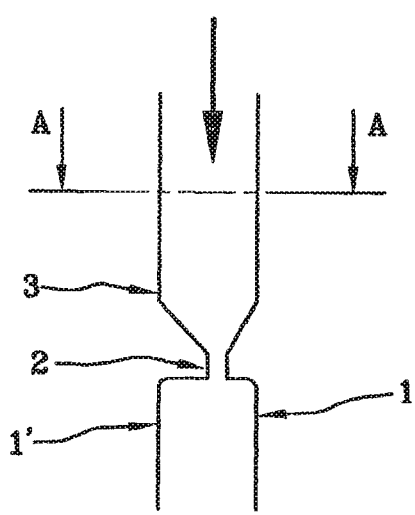

FIG. 15 shows the same site as in FIG. 13 with a non-axial narrowing.

Figure 16:
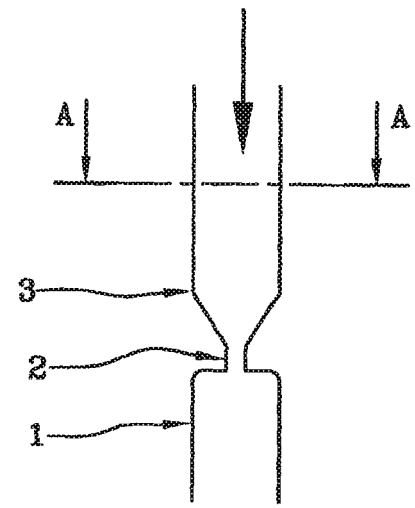

FIG. 16 shows the same site as in FIG. 13 with a square (and no longer round) passage section.

Each mode can be combined with another one for obtaining a further embodiment of the site.

Partial Separation(s):

Alternatively, the line according to the invention can have the first fluid passage means (224) of the turbulence area formation means (220) comprising at least a partial separation (250) whose longitudinal plane is perpendicular to the longitudinal axis of the first passage means (224). This is shown in FIGS. 17 to 22. The mode comprising a partial separation is shown in FIG. 17, when the partial separation concerned the pipe wall, and alternatively in FIG. 20 when the partial separation is centered with respect to the tube.

The turbulence area formation means (220) can comprise at least two partial separations (250) each longitudinal plane of which is perpendicular to the longitudinal axis of the first fluid passage means (224), divided according to a symmetry point located on said longitudinal axis. The mode including two partial separations is shown in FIG. 18 when the partial separations concern the pipe wall and, as shown in top view, the two separations substantially cover the whole of the pipe section. The mode including three partial separations is shown in FIG. 19 when the partial separations concern the pipe wall and, as shown in top view, the three separations substantially cover the whole of the pipe section. When several partial separations are used, these are distributed on the longitudinal axis of the pipe.

In FIGS. 17 to 22, three alternative position of the inlet of the secondary channel in the main channels of the site which blood gets through are shown with numerals 1, 1', 2, 2' and 3. "1" corresponds to injection straight downstream from the blood turbulence formation area; "1'", "2" and "2'" correspond to injection in the blood turbulence formation area, and "3" corresponds to injection straight upstream from the blood turbulence formation area.

More particularly, the secondary channel (230) for letting in the ion reestablishing solution in the site (145) can be integrated into one of the partial separations (250) and where the axis of the secondary channel is perpendicular to the longitudinal axis of the first fluid passage means (224). FIGS. 21 and 22 show this mode and differ in the outlet in the calcium injection site, located at the end of the partial separation transversally to blood sense (FIG. 21) or at the end of the partial separation parallel to blood sense and downstream from the narrowing.

It should be noted in general for all embodiments that injected calcium is not perturbed before its arrival in the main channel and that calcium is preferably let in by a pipe with a constant circular section, preferably with a smaller section than the one of the first and second main channels.

According to the invention, the turbulence area formation means (210) can be an elbow pipe or a straight pipe.

Moreover, the outlet of the secondary channel (230) of the infusion site is connected to the secondary inlet of the turbulence area formation means (210), this secondary inlet (232) being located on the second fluid passage means (224).

Distribution of Axes:

According to the invention:

the longitudinal axis of the secondary channel (230) of the site for letting in a solution reestablishing ion balance can be parallel to, preferably coaxial with the longitudinal axis of the second main channel of the site, the longitudinal axis of the secondary channel (230) of the site can be perpendicular to the longitudinal axis of the second main channel (220) of the site, the longitudinal axis of the first main channel (200) of the site can be perpendicular to the longitudinal axis of the second main channel (220) of the site, the longitudinal axis of the first channel (200) of the site can be parallel to, preferably coaxial with the longitudinal axis of the second main channel (220) of the site, the respective axes of the first (210) and of the second (220) main channel of the site and of the secondary channel (230) of the site can be coplanar, the longitudinal axis of the end of the first line portion (134) connected to the site is coaxial with the longitudinal axis of the first main channel (200) of the site, the longitudinal axis of the end of the second line portion (137) connected to the site is coaxial with the longitudinal axis of the second main channel (200) of the site.

The above generally implies that the inlet and outlet of each channel are included in the axis.

Furthermore, the invention can comprise the following elements:

the secondary channel (230) of the infusion site is connected to a bag or a syringe (133) containing liquid for reestablishing ion balance, the line comprises a bubble trap (111) acting on the first line portion (134) preferably upstream (possibly downstream) from the infusion site (145), the infusion site (145) is made as one piece, the infusion site (145) is made of rigid or semi-rigid hemocompatible plastic material, preferably starting from polyethylene terephthalate (PETG) or polytetrafluoroethylene (PTFE-Teflon), Dacron (polyester), PVC.

Moreover, the set of lines according to the invention, as well as the device for blood treatment according to the invention, can further include:

a container for local anticoagulation substance connected to the pre-infusion channel (109), and/or a container for solution reestablishing ion balance 133 (e.g. a bag, a syringe and so on) connected to the secondary channel (230) of the infusion site.

All lines can be disposable, the blood device too.

The blood treatment device according to the invention can further comprise one and/or the other of the following elements:

a drain channel (110) getting out of the second compartment (104) of the filter (102), a container of local anticoagulation substance connected to the pre-infusion channel (109), a container of solution reestablishing ion balance (133) connected to the secondary channel (230) of the infusion site, an air detector (113) acting on the blood line downstream from the infusion site (145), an air separator (111) on the blood line (108), upstream from the air detector.

By way of information, the infusion site shown in FIG. 3 has the following sizes:

| Side | High flow version (e.g. FIGS. 5, 6 and 7) | Low flow version (e.g. FIGS. 9 and 10) |
| --- | --- | --- |
| a | 6.55 | 4.75 |
| b | 4.15 | 2.87 |
| c | 3.18 | 3.18 |
| d | 0.80 | 0.80 |
| e | 9 | 9 |
| f | 6 | 6 |
| g | 1.2 | 0.8 |

FIGS. 6 and 7 also contain sizes to an indicative purpose. All these sizes are in no way limiting for the present description.

Advantages of the Invention

The invention has several advantages:

the device enables to homogenize blood and calcium injected, thus preventing any formation of local coagulation (generally observed as filament), it requires no additional component normally used in the extracorporeal blood circuit, the reestablishing solution (calcium in particular) is mixed with blood in a homogeneous manner and blood is not damaged by the turbulence area, the turbulence formation area is integrated into the disposable blood line: this is no additional means or a means independent from the extracorporeal circuit and it is not strictly necessary to use a syringe.

What is claimed is:

1. A method of anticoagulating blood treated during extracorporeal circulation in an extracorporeal circulation blood or plasma treatment device, the extracorporeal circulation blood or plasma treatment device comprising:

a filter having a first compartment and a second compartment separated by a semipermeable membrane;

an arterial line in fluid communication with the first compartment of the filter;

a pre-infusion channel for a local anticoagulation substance in fluid communication with the arterial line;

a container of a local anticoagulation substance in fluid communication with the pre-infusion channel;

a venous blood line in fluid communication with the first compartment of the filter, the venous blood line comprising:

a first line portion in fluid communication with an outlet of the filter, a second line portion in fluid communication with a patient's vascular access, an infusion site between the first line portion and the second line portion for injecting into the blood line a solution reestablishing blood or plasma ion balance, the infusion site comprising:

a first main channel in fluid communication with the first line portion and having a first passage section, a second main channel in fluid communication with the second line portion and having a second passage section, and a turbulence area downstream from and in fluid communication with the first main channel, and upstream from and in fluid communication with the second main channel, the turbulence area comprising a first fluid passage defining a reduction in passage section having a smallest passage section smaller than the first passage section and smaller than the second passage section, and a secondary channel comprising an inlet for the solution reestablishing blood or plasma ion balance and an outlet in fluid communication with at least one of the first main channel, the turbulence area and the second main channel; and a container of solution reestablishing blood or plasma ion balance in fluid communication with the secondary channel of the infusion site via a post-infusion line;

the method comprising:

a) flowing blood or plasma through the arterial line, b) infusing the local anticoagulation substance through the pre-infusion channel into the arterial line, c) filtering blood through the filter, d) flowing the filtered blood through the first line portion of the venous blood line, e) flowing the filtered blood in the turbulence area of the infusion site to cause a turbulence in blood flow, f) infusing the solution for reestablishing ion balance through the secondary channel of the infusion site, and g) flowing the filtered blood mixed with the solution for reestablishing blood or plasma ion balance through the second portion of the blood line, wherein step f) is carried out directly before, during or directly after step e).

2. The method of claim 1, wherein the post-infusion line is internally mounted into the secondary channel, an outer surface of the post-infusion line portion being sealingly connected to an inner surface of a post-infusion passage section of the infusion site.

3. The method of claim 1, wherein the first line portion is internally mounted into the first main channel of the infusion site and the second line portion is internally mounted into the second main channel of the infusion site.

4. The method of claim 1, wherein causing turbulence in blood flow includes switching from a laminar blood flow to a turbulent blood flow in the infusion site.

5. The method of claim 4, further including increasing the Reynolds number to switch from the laminar blood flow to the turbulent blood flow.

6. The method of claim 1, wherein causing turbulence in blood flow includes causing the blood flow to generate multiple whirlpools.

7. The method of claim 1, wherein at least one of the local anticoagulation substance includes citrate or the solution reestablishing blood or plasma ion balance includes calcium.

8. The method of claim 1, wherein the solution reestablishing blood or plasma ion balance is not perturbed before arrival in the at least one of the first main channel, the turbulence area or the second main channel.

9. The method of claim 1, comprising injecting the solution reestablishing blood or plasma ion balance using a pipe having a constant circular section, the constant circular section of the pipe being smaller than any of the sections of the first main channel and the second main channel.

10. The method of claim 1, wherein the turbulence area includes a second fluid passage downstream from the first fluid passage and defining an increase in fluid passage section, and wherein the largest fluid passage section of the second fluid passage is smaller than said first passage section and smaller than said second passage section.

11. The method of claim 10, wherein the increase in fluid passage section of the second fluid passage defines a shoulder perpendicular to the longitudinal axis of the second fluid passage.

12. The method of claim 1, wherein the first fluid passage of the turbulence area defines a continuous section narrowing fluid passage.

13. The method of claim 1, wherein the first fluid passage of the turbulence area has a constantly narrowing internal circular section, resulting in a conical internal surface having a symmetrical axis which is the longitudinal axis of the first passage.

14. The method of claim 13, wherein the Reynolds number for blood flow in the smallest circular section of the conical internal surface varies from 350 to 3,000.

15. The method of claim 13, wherein the Reynolds number for blood flow in the smallest circular section of the conical internal surface varies from 500 to 2,000.

16. The method of claim 13, wherein a ratio between the largest circular section of the conical internal surface and the smallest circular section of the conical internal surface is less than 3.6:1.

17. The method of claim 13, wherein the diameter of the smallest circular section of the conical internal surface is equal to or less than 1.2 mm.

18. The method of claim 1, wherein the diameter of an outlet of the secondary channel of the infusion site is equal to or less than 0.8 mm.

19. The method of claim 1, wherein a ratio between a diameter of the smallest passage section of the first fluid passage and a diameter of the first passage section is less than about 30%.

20. The method of claim 1, wherein the inlet of the secondary channel of the infusion site is tapered.

21. The method of claim 1, wherein the secondary channel section interposed between the inlet and the outlet has a constant circular section.

22. The method of claim 1, wherein the container of solution reestablishing blood or plasma ion balance is a bag or a syringe.

23. The method of claim 1, wherein the treatment device includes a bubble trap located along the venous blood line upstream from the infusion site.

24. The method of claim 1, wherein the treatment device includes an air detector operating with the venous blood line downstream from the infusion site.

* * * * *